US007769448B1

(12) United States Patent
Lu

(10) Patent No.: US 7,769,448 B1
(45) Date of Patent: Aug. 3, 2010

(54) MULTI-SITE CARDIAC STIMULATION DEVICE FOR CONTROLLING INTER-CHAMBER STIMULATION DELAY

(75) Inventor: Richard Lu, Medina, MN (US)

(73) Assignee: Pacesetter, Inc., Sylmar, CA (US)

( * ) Notice: Subject to any disclaimer, the term of this patent is extended or adjusted under 35 U.S.C. 154(b) by 979 days.

(21) Appl. No.: 11/124,308

(22) Filed: May 6, 2005

Related U.S. Application Data

(63) Continuation of application No. 09/930,725, filed on Aug. 14, 2001, now Pat. No. 6,937,895, which is a continuation-in-part of application No. 09/471,788, filed on Dec. 23, 1999, now Pat. No. 6,519,493.

(51) Int. Cl.
*A61N 1/08* (2006.01)

(52) U.S. Cl. ......................................................... 607/9

(58) Field of Classification Search ................. 600/373, 600/374, 377, 393, 509, 519; 607/4, 5, 6, 607/7, 9, 17, 28, 116, 122, 11
See application file for complete search history.

(56) References Cited

U.S. PATENT DOCUMENTS

| 5,350,410 | A |   | 9/1994  | Kleks et al. ..................... 607/28 |
|-----------|---|---|---------|------------------------------------------|
| 5,514,162 | A |   | 5/1996  | Bornzin et al. .................. 607/19 |
| 5,720,768 | A |   | 2/1998  | Verboven-Nelissen ........... 607/9 |
| 5,725,562 | A |   | 3/1998  | Sheldon ........................... 607/19 |
| 5,814,085 | A |   | 9/1998  | Hill ................................ 607/14 |
| 5,824,019 | A | * | 10/1998 | Rueter et al. ..................... 607/17 |
| 5,902,324 | A |   | 5/1999  | Thompson et al. ............... 607/9 |
| 5,951,593 | A |   | 9/1999  | Lu et al. .......................... 607/14 |
| 5,964,788 | A |   | 10/1999 | Greenhut ......................... 607/17 |
| 6,026,324 | A |   | 2/2000  | Carlsson ......................... 607/27 |
| 6,070,100 | A | * | 5/2000  | Bakels et al. .................... 607/9 |
| 6,081,748 | A |   | 6/2000  | Struble et al. ................... 607/9 |
| 6,512,953 | B2| * | 1/2003  | Florio et al. .................... 607/28 |
| 6,519,493 | B1|   | 2/2003  | Florio et al. .................... 607/9 |
| 6,567,700 | B1|   | 5/2003  | Turcott et al. ................... 607/9 |
| 7,142,918 | B2| * | 11/2006 | Stahmann et al. ............... 607/15 |

FOREIGN PATENT DOCUMENTS

WO    WO 99/ 30777    6/1999

OTHER PUBLICATIONS

Cazeau S. et al., "Four Chamber Pacing in Dilated Cardiomyopathy," PACE, vol. 17, (Nov. 1994, Part II), pp. 1974-1979.
Misier Arnand R. Ramdat. MD, PhD. et al., "Multisite or Alternate Site Pacing for the Prevention of Atrial Fibrillation," American Journal of Cardiology, vol. 83(5B)(Mar. 11, 1999), pp. 237D-240D.

* cited by examiner

*Primary Examiner*—Carl H Layno
*Assistant Examiner*—Frances P Oropeza

(57) ABSTRACT

An implantable, multi-chamber cardiac stimulation device and method automatically adjust inter-chamber stimulation delays whenever stimulation rate is changed according to a patient's metabolic need. Inter-chamber stimulation delays include inter-atrial delays, inter-ventricular delays, and atrio-ventricular delays. Inter-chamber stimulation delays are defined according to whether the event which triggers the start of the delay is an intrinsic sensed event or the delivery of a stimulation pulse. Adjustment to inter-chamber stimulation delays is made as a function of the stimulation rate changes. By providing automatically adjustable inter-chamber stimulation delays optimal synchronization of heart chamber contractions may be maintained at all stimulation rates.

20 Claims, 3 Drawing Sheets

MULTI-SITE CARDIAC STIMULATION DEVICE FOR CONTROLLING INTER-CHAMBER STIMULATION DELAY

CROSS-REFERENCE TO RELATED APPLICATIONS

This application is a continuation of U.S. patent application Ser. No. 09/930,725, filed Aug. 14, 2001 now U.S. Pat. No. 6,937,895, which is a continuation-in-part of U.S. patent application Ser. No. 09/471,788, filed on Dec. 23, 1999, now U.S. Pat. No. 6,519,493; and is related to U.S. patent application Ser. No. 09/904,159, filed Jul. 11, 2001, now U.S. Pat. No. 6,477,417, and to U.S. patent application Ser. No. 09/850,560, filed May 7, 2001, now U.S. Pat. No. 6,654,639; all of which are incorporated herein by reference.

FIELD OF THE INVENTION

The present invention relates generally to programmable cardiac stimulating devices. More specifically, this invention is directed to an implantable, multi-chamber cardiac stimulation device and associated method, for controlling the inter-chamber stimulation delay between the atrial and/or ventricular chambers.

BACKGROUND OF THE INVENTION

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or other anti-arrhythmia therapies to the heart, via electrodes implanted in contact with the heart tissue, at a desired energy and rate. One or more heart chambers may be electrically stimulated depending on the location and severity of the conduction disorder.

A single-chamber pacemaker delivers pacing pulses to one chamber of the heart, either one atrium or one ventricle. Dual chamber pacemakers are now commonly available and can provide stimulation in both an atrial chamber and a ventricular chamber, typically the right atrium and the right ventricle. Both unipolar or bipolar dual chamber pacemakers exist in which a unipolar or bipolar lead extends from an atrial channel of the dual chamber device to the desired atrium (e.g. the right atrium), and a separate unipolar or bipolar lead extends from a ventricular channel to the corresponding ventricle (e.g. the right ventricle). In dual chamber, demand-type pacemakers, commonly referred to as DDD pacemakers, each atrial and ventricular channel includes a sense amplifier to detect cardiac activity in the respective chamber and an output circuit for delivering stimulation pulses to the respective chamber.

If an intrinsic atrial depolarization signal (a P-wave) is not detected by the atrial channel, a stimulating pulse will be delivered to depolarize the atrium and cause contraction. Following either a detected P-wave or an atrial pacing pulse, the ventricular channel attempts to detect a depolarization signal in the ventricle, known as an R-wave. If no R-wave is detected within a defined atrio-ventricular interval (AV interval or delay), a stimulation pulse is delivered to the ventricle to cause ventricular contraction. In this way, rhythmic dual chamber pacing is achieved by coordinating the delivery of ventricular output in response to a sensed or paced atrial event.

Early pacemakers stimulated the heart at a fixed rate. Rate-responsive pacemakers were developed in order to provide an adaptable stimulation rate responsive to the physical need of the patient. An implanted rate-responsive pacemaker (or implantable cardioverter defibrillator having rate-responsive pacing capabilities) typically operates to maintain a predetermined minimum heart rate when the patient is engaged in physical activity at or below a threshold level, and gradually increases the maintained heart rate in accordance with increases in physical activity until a maximum rate is reached. Thus, such rate-responsive pacemakers typically include processing circuitry that correlates measured physical activity to an appropriate heart rate. In many rate-responsive pacemakers, the minimum heart rate, maximum heart rate and the transition rates between the minimum and maximum heart rates are parameters that may be telemetrically adjusted to meet the needs of a particular patient.

Most rate-responsive pacemakers employ sensors that transduce mechanical forces associated with physical activity to determine the level of metabolic need of a patient, relying upon the clinical association of body motion with increasing levels of exercise. These activity sensors generally contain a piezoelectric transducing element that generates a measurable electrical potential when a mechanical stress resulting from physical activity is experienced by the sensor. Thus, by analyzing the signal from a piezoelectric activity sensor, a rate-responsive pacemaker can determine how frequently pacing pulses should be applied to the patient's heart. Reference is made to U.S. Pat. No. 5,514,162 to Bornzin et al.

Other physiological sensors frequently used in rate-responsive pacemakers are respiration sensors. Such sensors may be employed to measure respiratory rate, tidal volume, or the product of these two parameters, minute ventilation. Each of these parameters increases in proportion to changes in carbon dioxide production associated with physical activity. Minute ventilation-sensing, rate-adaptive pacing systems have been demonstrated to provide rate modulation that is closely correlated with oxygen consumption in most patients implanted with these devices. Reference is made to U.S. Pat. No. 5,964,788 to Greenhut.

In dual chamber pacemakers (or implantable cardioverter defibrillators), pacing rate may be based on a ventricular stimulation rate or an atrial stimulation rate with the interval between atrial and ventricular stimulation determined by a programmable atrioventricular delay (AV delay or AV interval). In a healthy heart, the interval between an atrial P-wave and a ventricular R-wave varies as heart rate varies. Thus to provide rate-responsive stimulation that is more physiological, rate responsive pacemakers having an adjustable AV interval have been developed. By adjusting the AV interval, appropriate AV synchrony may be maintained as the pacing rate is varied according to the physiological sensor output. Adjustment of the AV interval can be advantageous in maximizing cardiac output or in ensuring ventricular pacing occurs when pacing control of the heart rate is desired.

Mounting clinical evidence supports the evolution of more complex cardiac stimulating devices capable of stimulating three or even all four heart chambers to stabilize arrhythmias or to re-synchronize heart chamber contractions (Ref: Cazeau S. et al., "Four chamber pacing in dilated cardiomyopathy," Pacing Clin. Electrophsyiol. 1994 17(11 Pt 2):1974-9). Stimulation of multiple sites within a heart chamber has also been found effective in controlling arrhythmogenic depolarizations (Ref: Ramdat-Misier A., et al., "Multisite or alternate site pacing for the prevention of atrial fibrillation," Am. J. Cardiol., 1999 11;83(5b):237D-240D).

In order to achieve multi-chamber or multi-site stimulation in a clinical setting, conventional dual-chamber pacemakers have now been used in conjunction with adapters that couple together two leads going to different pacing sites or heart chambers. Reference is made Cazeau et al. (Pacing Clin. Electrophsyiol. 1994 17(11 Pt 2):1974-9) that describes a four chamber pacing system in which unipolar right and left atrial leads are connected via a bifurcated bipolar adapter to the atrial port of a bipolar dual chamber pacemaker. Likewise, unipolar right and left ventricular leads are connected via a bifurcated bipolar adapter to the ventricular channel. The left chamber leads were connected to the anode terminals and the right chamber leads were connected to the cathode terminals of the dual chamber device. In this way, simultaneous bi-atrial or simultaneous bi-ventricular pacing is achieved via bipolar stimulation but with several limitations.

One limitation of the multi-chamber stimulation systems described above is that simultaneous stimulation of left and right chambers, as required when two leads are coupled together by one adapter, is not always necessary or desirable. For example, in some patients, conduction between the two atria may be compromised, however the pacemaking function of the sinus node in the right atrium may still be normal. Hence, detection of an intrinsic depolarization in the right atrium could be used to trigger delivery of a pacing pulse in the left atrium. Since an intrinsic depolarization has occurred in one chamber, simultaneous stimulation of both chambers in this situation is unnecessary.

In another example, when inter-atrial or inter-ventricular conduction is intact, stimulation in one chamber may be conducted naturally to depolarize the second chamber. A stimulation pulse delivered in one chamber, using the minimum energy required to depolarize that chamber, will be conducted to the opposing chamber thus depolarizing both chambers. In this case, stimulation of both chambers simultaneously would be wasteful of battery energy.

In the presence of an inter-atrial or inter-ventricular conduction defect, one may want to control the interval between a sensed or paced event in one chamber and delivery of a stimulation pulse to the other chamber. If pacing is required in both the left and right chambers, the control of the sequence of the stimulation pulse delivery to each chamber, rather than the simultaneous delivery of stimulation pulses, may be necessary in order to achieve a specific activation sequence that has hemodynamic benefit.

Even in patients with intact conduction, it may be desirable to precisely control the activation sequence of the heart chambers in order to provide maximum hemodynamic benefit. Precise control of the activation sequence may improve the coordination of heart chamber contractions resulting in more effective filling and ejection of blood from the heart.

In certain currently available devices, adapters are no longer required. The connection between leads is hardwired internally in the connector block coupling the ventricular leads to the ventricular channel and the atrial leads to the atrial channel. While this design advantageously eliminates the need for adapters, the hardware connections preclude the introduction of separate timing between stimulation pulses delivered to each chamber or responding with any programmable delays to a sensed event by delivery of an output pulse to the other chamber.

To address some of these limitations, multichamber stimulation devices have been proposed that allow some degree of independent stimulation and/or sensing of different chambers of the heart. Reference is made, for example, to U.S. Pat. No. 5,720,768 to Verboven-Nelissen, U.S. Pat. No. 5,902,324 to Thompson et al., U.S. Pat. No. 6,081,748 to Struble et al.

To further enhance the benefit provided to the patient during periods of exercise or increased metabolic demand, it would be desirable to allow the inter-chamber stimulation intervals to be automatically adjusted as changes in stimulation rate occur in response to a physiological sensor of metabolic need, or in response to algorithmic adjustments. Therefore, what is needed is a multi-chamber stimulation device that provides programmable inter-chamber timing intervals that are also automatically adjusted as a function of the changing stimulation rate.

SUMMARY OF THE INVENTION

The present invention addresses this need by providing a multichamber cardiac stimulation device and method for automatically adjusting inter-chamber stimulation delays in response to changes in stimulation rate, for example, based on a sensor-indicated, rate-responsive change in the stimulation rate. Alternatively, the stimulation rate may change based on algorithmic adjustments to the stimulation rate. Examples of such algorithms include dynamic atrial overdrive, vasovagal response, orthostatic response, and the like.

The foregoing and other features of the present invention are realized by providing an implantable, rate-responsive multichamber cardiac stimulation device equipped with cardiac data acquisition capabilities. A preferred embodiment of the stimulation device includes a control system for controlling the operation of the device and executing various test algorithms; a set of leads for receiving cardiac signals and for delivering atrial and ventricular stimulation pulses; a set of sensing circuits comprised of sense amplifiers for sensing and amplifying the cardiac signals; a sampler, such as an A/D converter for sampling cardiac signals; and pulse generators for generating atrial and ventricular stimulation pulses.

The device is preferably equipped with a physiological sensor for indicating changes in metabolic demand or activity such that the stimulation rate may be automatically adjusted according to metabolic need. In addition, the device includes memory for storing operational parameters for the control system, such as stimulation parameter settings, timing intervals and sensing parameter settings. The device also includes a telemetry circuit for communicating with an external programmer.

When operating according to a preferred embodiment, the control system determines when a change is needed in the stimulation rate and, based on this rate change, adjusts inter-chamber stimulation delays accordingly. Inter-chamber stimulation delays determine the time-out interval between a sensed or stimulated event in one chamber, which triggers the start of the inter-chamber delay, and the delivery of a stimulation pulse in another chamber. Therefore, inter-chamber stimulation delays may include inter-atrial delays, inter-ventricular delays, and atrio-ventricular delays. Inter-chamber delays may be uniquely defined depending on whether the triggering event is a sensed event or a stimulated event and whether the triggering event has occurred in the left chamber or in the right chamber.

By providing automatically adjustable inter-chamber stimulation delays, a multichamber cardiac stimulation device is capable of adjusting stimulation rate in response to metabolic need, and still maintains optimal synchronization of heart chambers. The present invention is thus expected to improve the therapeutic benefit provided by a multichamber stimulation device.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF THE PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout.

The present invention is directed at providing automatic adjustment of interchamber stimulation delays in a rate-responsive, multichamber cardiac stimulation device. A general cardiac stimulation device will thus be described in conjunction with FIGS. 1 and 2, in which the features included in the present invention could be implemented. It is recognized, however, that numerous variations of such a device exist in which the methods presented herein could be implemented without deviating from the scope of the present invention.

Figure 1:
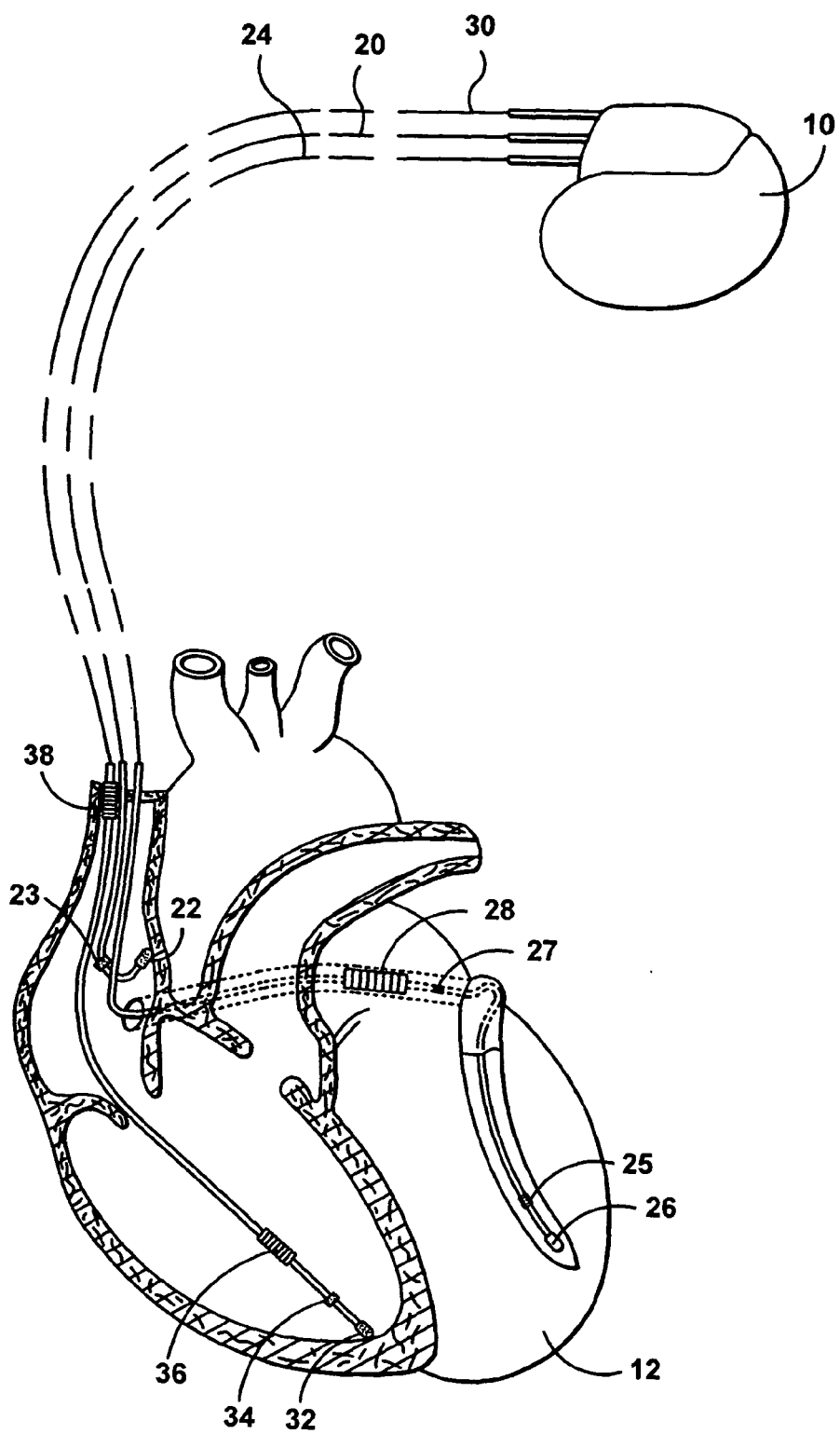
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a coronary sinus tip electrode 26 for unipolar stimulation or in combination with left ventricular ring electrode 25 for bipolar stimulation, left atrial pacing therapy using at least a coronary sinus ring electrode 27, and shocking therapy using at least a coronary sinus coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

Figure 2:
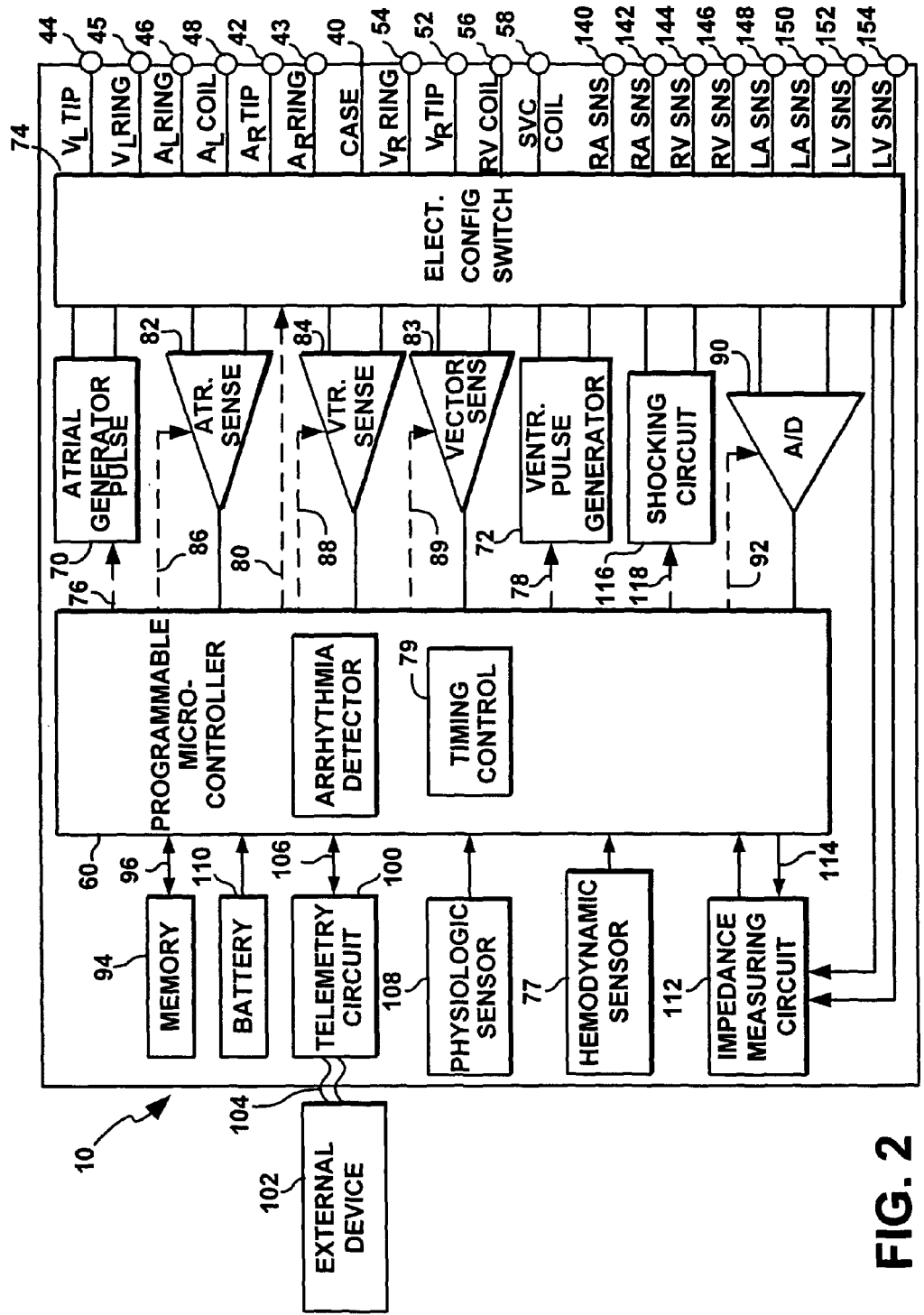
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for defibrillation shocking purposes.

The stimulation device 10 further includes a connector having a plurality of terminals 42, 43, 44, 45, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal ($A_R$ TIP) 42 adapted for connection to the atrial tip electrode 22. The connector may also include a right atrial ring terminal ($A_R$ RING) 43 for connection to the atrial ring electrode 23.

To achieve left chamber sensing, pacing, and shocking, the connector includes at least a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, which are adapted for connection to the coronary tip electrode 26, the left ventricular ring electrode 25, the coronary sinus ring electrode 27, and the coronary sinus coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g. unipolar, bipolar, cross-chamber, etc.) by selectively closing the appropriate combination of switches (not shown) as is known in the art. Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". When automatic capture is enabled, the microcontroller 60 searches for a depolarization signal following a stimulation pulse during a "detection window" set by timing control circuitry 79 within microcontroller 60. The microcontroller 60 enables the data acquisition system 90 via control signal 92 to sample the cardiac signal that falls in the capture detection window. The sampled signal is evaluated to determine if it is an evoked response signal based on its amplitude, peak slope, or another signal feature or combination of features. The detection of an evoked response during the detection window indicates that capture has occurred.

Capture detection may occur on a beat-by-beat basis or on a sampled basis. When loss of capture is detected, a safety, back-up pulse is delivered shortly after the primary pulse in order to prevent asystole. Preferably, a capture threshold search is then performed in order to re-determine the threshold and appropriately adjust the stimulation pulse output. A capture threshold search may also be performed on a periodic basis, preferably once a day during at least the acute phase (e.g., the first 30 days) and less frequently thereafter. A capture threshold search would begin at a desired starting point (either a high output level or the level at which capture is currently occurring) and continue by decreasing the output level until capture is lost. The output level is then increased again until capture is regained. The lowest output level at which sustained capture is regained is known as the capture threshold. Thereafter, the stimulation output is adjusted to a level equal to the capture threshold plus a working margin. The implementation of capture detection circuitry and algorithms is described for example, in U.S. Pat. No. 5,350,410 to Kleks et al.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 includes a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters, such as the rate at which the atrial and ventricular pulse generators 70 and 72 generate stimulation pulses. In accordance with the present invention inter-chamber stimulation delays will be adjusted appropriately as the rate is adjusted.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 μA, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 which is enabled by the microcontroller 60 by means of a control signal 114.

It is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high (11 to 40 Joules) energy, as controlled by the microcontroller 60. Such shocking pulses are applied to the patient's heart through at least two shocking electrodes, and as shown in this embodiment, selected from the coronary sinus coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the coronary sinus coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
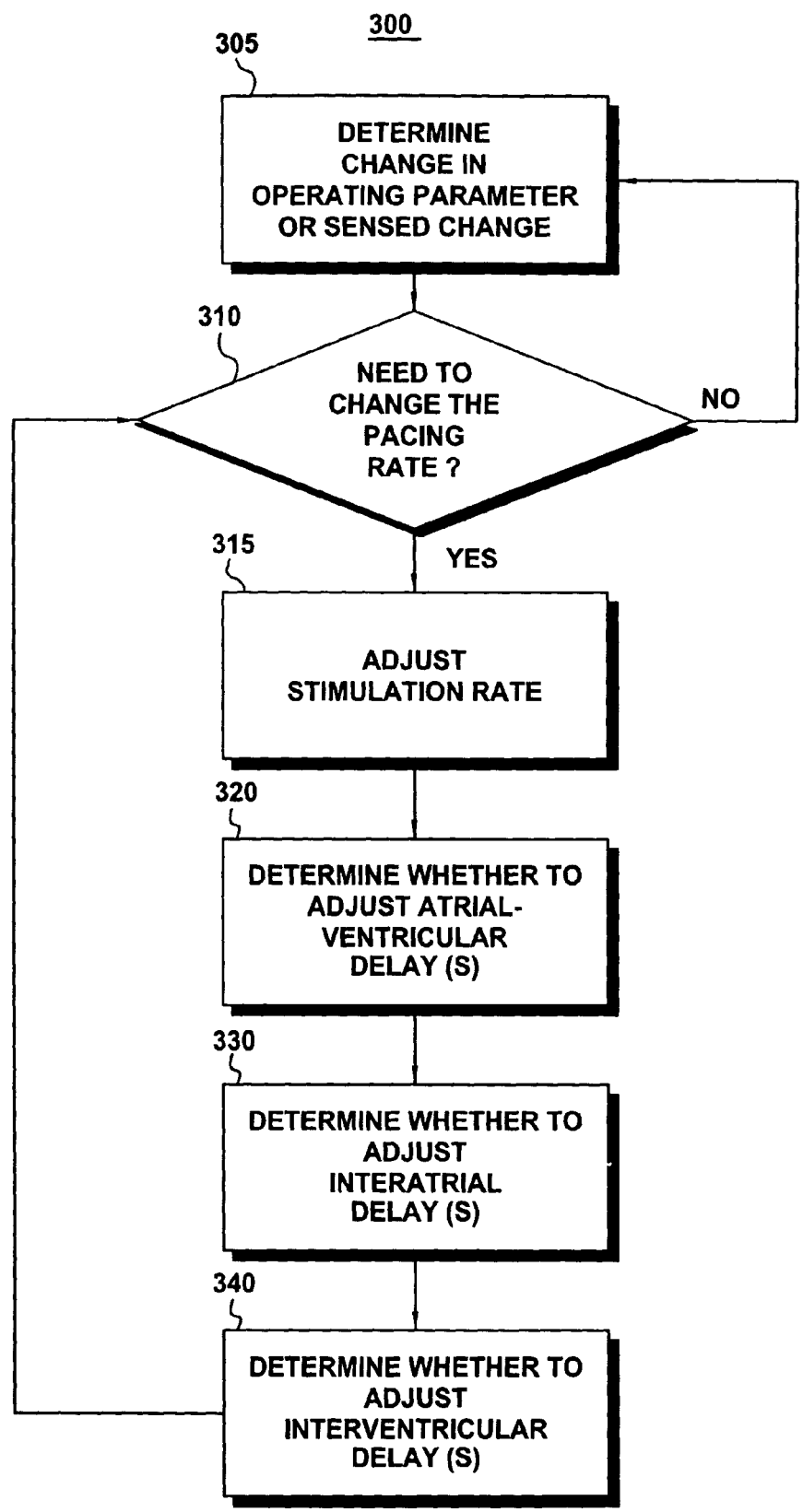
FIG. 3 is a flow chart providing an overview of the operation of the present invention for automatically adjusting the inter-chamber delay intervals in the stimulation device of FIGS. 2 and 3.

FIG. 3 depicts a method 300 that illustrates the operation and novel features implemented in one embodiment of the device 10 for automatically adjusting inter-chamber stimulation delays. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

At step 305, the microcontroller 60 determines a change in some operating parameter. In one embodiment, the change is indicated by physiological sensor 108 and corresponds to a rate-responsive change. Alternatively, the change may be due to an algorithmic adjustment, such as atrial overdrive pacing, vasovagal response, orthostatic response, and the like (hereinafter referred to as "algorithm-based changes").

If, at decision step 310, method 300 determines that a change in the stimulating rate is required, microprocessor 60 automatically adjusts the rate at step 315 and proceeds to adjust any applicable inter-chamber delays, starting at step 320. If however, method 300 determines at decision step 310 that a change in the rate is not required, it returns to step 305.

At step 320, method 300 adjusts one or more inter-chamber delays. This adjustment includes for example: a delay between a sensed or stimulated event in the right atrium and delivery of a stimulation pulse in the right ventricle; a delay between an event in the right atrium and a stimulation pulse in the left ventricle; a delay between an event in the left atrium and delivery of a stimulation pulse to the right ventricle; and a delay between a left atrial event and a left ventricular stimulation pulse. Furthermore, each of these delays may be defined separately according to whether the triggering event starting the atrio-ventricular delay is a sensed event or an atrial stimulation pulse. Thus, in the embodiment shown in FIG. 1, at least eight possible atrio-ventricular delays may be adjusted at step 320. These eight possibilities are listed in TABLE I below.

In TABLE I below, each delay is referred to by a four-letter code. The first pair of letters indicates the triggering event that initiates the delay: the first letter indicates the right or left chamber by an "R" or an "L," respectively, and the second letter indicates an atrial stimulation "A", an atrial sense "P", a ventricular stimulation "V" or a ventricular sense "R." The second pair of letters indicates which chamber will be stimulated upon expiration of the delay if no intervening intrinsic event is sensed in that chamber: right atrium is indicated by "RA"; left atrium, "LA"; right ventricle, "RV"; and left ventricle, "LV."

TABLE I

| INTER-CHAMBER DELAY | TRIGGERING EVENT: | CHAMBER TO BE STIMULATED AT EXPIRATION OF DELAY: |
|---|---|---|
| Atrio-ventricular: | | |
| 1. RA-RV delay | Right atrial stimulation | Right ventricle |
| 2. RA-LV delay | Right atrial stimulation | Left ventricle |
| 3. RP-RV delay | Right atrial sense | Right ventricle |
| 4. RP-LV delay | Right atrial sense | Left ventricle |
| 5. LA-RV delay | Left atrial stimulation | Right ventricle |
| 6. LA-LV delay | Left atrial stimulation | Left ventricle |
| 7. LP-RV delay | Left atrial sense | Right ventricle |
| 8. LP-LV delay | Left atrial sense | Left ventricle |
| Inter-atrial: | | |
| RA-LA delay | Right atrial stimulation | Left atrium |
| LA-RA delay | Left atrial stimulation | Right atrium |
| RP-LA delay | Right atrial sense | Left atrium |
| LP-RA delay | Left atrial sense | Right atrium |
| Inter-ventricular: | | |
| RV-LV delay | Right ventricular stimulation | Left ventricle |
| LV-RV delay | Left ventricular stimulation | Right ventricle |
| RR-LV delay | Right ventricular sense | Left ventricle |
| LR-RV delay | Left ventricular sense | Right ventricle |

At step 330, the inter-atrial delays may be adjusted. This adjustment may include: a right atrial to left atrial delay, and a left atrial to right atrial delay. Separate delays may be defined according to whether the triggering event is a sensed atrial event or an atrial stimulation pulse. Thus, in the embodiment shown in FIG. 1, at least four possible inter-atrial delays, which are listed in TABLE I, may be adjusted at step 330.

At step 340, the inter-ventricular delays may be adjusted. A right ventricle to left ventricle delay and a left ventricle to right ventricle delay may be adjusted, including separate delays defined for a ventricular sensed event or a ventricular stimulation pulse as the triggering event. At least four possible inter-ventricular delays listed in TABLE I may be adjusted in the embodiment shown in FIG. 1.

Each of the adjustments to the inter-chamber delays made at steps 320 to 340 are made according to a predetermined function of the change in stimulation rate. For example, the inter-chamber delays may each be defined as a percentage of the total cardiac cycle. If the base stimulation rate is increased in response to an increase in metabolic need such that each cardiac cycle is shortened by 100 msec, and an atrio-ventricular delay is set to be equal to 28% of the cardiac cycle, then the atrio-ventricular delay will be shortened by 28 ms. It will be understood that various other functional relationships may be utilized, as will be apparent to those skilled in the art.

Alternatively, the base stimulation rate and the atrio-ventricular (inter-chamber) delay could be linearly related within a maximum limit and a minimum limit. A sensor, such as a hemodynamic sensor 77 (FIG. 2) could be used to determine the maximum and minimum limits of the atrio-ventricular delay. In another alternative embodiment, the inter-chamber delay could be a predetermined percentage of the stimulation rate (or a change in the stimulation rate).

Other functions may define the overall relation of the inter-atrial, inter-ventricular, and atrio-ventricular delays to the cardiac cycle duration such that each are adjusted appropriate to a change in stimulation rate. These functions are intended to maintain a desired synchronization of the heart chambers such that hemodynamic efficiency is maximized at any stimulation rate.

Moreover, while the invention has been described primarily in connection with changes in stimulation rates based on a rate-responsive device, it will be understood that the invention is not limited to such an embodiment. For example, as described above, the invention has utility in connection with algorithm-based changes to the stimulation rate, such as changes resulting from an overdrive pacing algorithm, a vasovagal response algorithm, an orthostatic compensation pacing algorithm, and other such pacing algorithms.

Thus, a system and method have been described for automatically adjusting inter-chamber delays in a rate-responsive multichamber cardiac stimulation device. By providing automatically adjustable inter-chamber delays, optimal synchronization of heart chambers may be maintained during changing stimulation rate in response to changing metabolic need.

While detailed descriptions of specific embodiments of the present invention have been provided, it would be apparent to those reasonably skilled in the art that numerous variations of the methods described herein are possible in which the concepts of the present invention may readily be applied. As an example, while the present invention is described as being directed toward a rate responsive application, the present method of adapting the inter-chamber delay as a function of rate could also in an overdrive pacing mode. The descriptions provided herein are for the sake of illustration and are not intended to be exclusive.

What is claimed is:

1. A method of automatically adjusting an inter-ventricular stimulation delay for use in a multichamber cardiac stimulation device, the method comprising:
   selectively adjusting a stimulation rate; and
   in response to every adjustment of the stimulation rate, automatically adjusting the inter-ventricular stimulation delay as a function of the stimulation rate, wherein the inter-ventricular stimulation delay is the delay between an event in the right ventricle and a stimulation pulse delivered to the left ventricle.

2. The method of claim 1, wherein the step of selectively adjusting the stimulation rate includes causing a sensed event to trigger the automatic adjustment of the inter-ventricular stimulation delay.

3. The method of claim 1, wherein the step of selectively adjusting the stimulation rate includes causing an algorithmic adjustment to trigger the automatic adjustment of the inter-ventricular stimulation delay.

4. The method of claim 1, wherein automatically adjusting the inter-ventricular stimulation delay comprises adjusting an inter-chamber delay between a right ventricular sensed event and a left ventricular stimulation pulse.

5. The method of claim 1, wherein automatically adjusting the inter-ventricular stimulation delay comprises adjusting an inter-chamber delay between a right ventricular stimulation pulse and a left ventricular stimulation pulse.

6. The method of claim 1, wherein automatically adjusting the inter-ventricular stimulation delay comprises adjusting an inter-chamber delay between a left ventricular sensed event and a right ventricular stimulation pulse.

7. The method of claim 1, wherein automatically adjusting the inter-ventricular stimulation delay comprises adjusting an inter-chamber delay between a left ventricular stimulation pulse and a right ventricular stimulation pulse.

8. The method of claim 1, further comprising delivering stimulation pulses to a heart chamber upon the expiration of an adjusted inter-ventricular stimulation delay so that a desired synchronization of heart chamber contractions is maintained when a heart stimulation rate is changed.

9. A multichamber cardiac stimulation device for automatically adjusting inter-ventricular delays, comprising:
- a pulse generator that selectively generates stimulation pulses;
- at least one lead, connected to the pulse generator, that delivers the stimulation pulses to one or more cardiac chambers;
- a sensor that senses physiologic activity and generates sense signals;
- control circuitry that is responsive to the sense signals to adjust the stimulation rate; and
- a timing circuit, responsive to every adjustment of the stimulation rate, to automatically adjust the inter-ventricular stimulation delay as a function of the stimulation rate, wherein the inter-ventricular stimulation delay is the delay between an event in the right ventricle and a stimulation pulse delivered to the left ventricle.

10. The stimulation device of claim 9, wherein the stimulation rate change is triggered by a sensed event.

11. The stimulation device of claim 9, wherein the stimulation rate change is triggered by a stimulation pulse.

12. The stimulation device of claim 9, wherein the inter-ventricular delay is a delay between at least one of:
- a right ventricular sensed event and a left ventricular stimulation pulse;
- a right ventricular stimulation pulse and a left ventricular stimulation pulse;
- a left ventricular sensed event and a right ventricular stimulation pulse; and
- a left ventricular stimulation pulse and a right ventricular stimulation pulse.

13. The stimulation device of claim 9, wherein the timing circuit automatically adjusts the inter-ventricular stimulation delay as a linear function of the stimulation rate.

14. The stimulation device of claim 9, wherein the timing circuit automatically adjusts the inter-ventricular stimulation delay as a predetermined percentage of the stimulation rate.

15. A multichamber cardiac stimulation device for automatically adjusting inter-ventricular delays, comprising:
- means for selectively adjusting a stimulation rate; and
- means, responsive to every adjustment in the stimulation rate, for automatically adjusting an inter-ventricular stimulation delay as a function of the stimulation rate, wherein the inter-ventricular stimulation delay is the delay between an event in the right ventricle and a stimulation pulse delivered to the left ventricle.

16. The stimulation device of claim 15, wherein the stimulation rate change is triggered by a sensed event.

17. The stimulation device of claim 15, wherein the stimulation rate change is triggered by a stimulation pulse.

18. The stimulation device of claim 15, wherein the inter-ventricular delay is a delay between:
- a right ventricular sensed event and a left ventricular stimulation pulse;
- a right ventricular stimulation pulse and a left ventricular stimulation pulse;
- a left ventricular sensed event and a right ventricular stimulation pulse; or
- a left ventricular stimulation pulse and a right ventricular stimulation pulse.

19. A multichamber cardiac stimulation device comprising:
- a pulse generator that selectively generates stimulation pulses;
- at least one lead configured for connection to the pulse generator, and that is operative to deliver the stimulation pulses to one or more cardiac chambers;
- a control circuit that is programmed with one or more pacing algorithms to control a stimulation rate; and
- a timing circuit that is responsive to every change in the stimulation rate to automatically adjust an inter-ventricular stimulation delay as a function of the stimulation rate change, wherein the inter-ventricular stimulation delay is the delay between an event in the right ventricle and a stimulation pulse delivered to the left ventricle.

20. The stimulation device of claim 19, wherein the inter-ventricular delay is a delay between at least one of:
- a right ventricular sensed event and a left ventricular stimulation pulse;
- a right ventricular stimulation pulse and a left ventricular stimulation pulse;
- a left ventricular sensed event and a right ventricular stimulation pulse; or
- a left ventricular stimulation pulse and a right ventricular stimulation pulse.

* * * * *